United States Patent [19]

Scherrer

[11] 4,141,990

[45] Feb. 27, 1979

[54] ANTI-MICROBIAL ALKYL SUBSTITUTED-2-NITRO-3-PHENYLBENZOFURANS

[75] Inventor: Robert A. Scherrer, White Bear Lake, Minn.

[73] Assignee: Riker Laboratories, Inc., Northridge, Calif.

[21] Appl. No.: 445,976

[22] Filed: Feb. 26, 1974

[51] Int. Cl.$^2$ .................... A61L 9/00; C07D 307/82
[52] U.S. Cl. ................................ 424/285; 260/346.22
[58] Field of Search .................. 264/346.2 R; 424/285

[56] References Cited
PUBLICATIONS

Royer et al., Chem. Abstr. (1973), vol. 79, 91862c.
Abstract of Royer et al., Chim. Ther. (1973), vol. 8 (2), pp. 139-142.
Stoermer, Berichte, vol. 44, (1911), pp. 1853-1865, (Chemical Abstr., vol. 5 (1911), pp. 3262-3264).

Primary Examiner—Henry R. Jiles
Assistant Examiner—Bernard Dentz
Attorney, Agent, or Firm—Cruzan Alexander; Donald M. Sell; Donald C. Gipple

[57] ABSTRACT

Methyl-substituted-2-nitro-3-phenylbenzofurans are prepared from methyl-substituted-3-phenylbenzofurans and are found to be useful antimicrobial agents.

13 Claims, No Drawings

ANTI-MICROBIAL ALKYL SUBSTITUTED-2-NITRO-3-PHENYLBENZOFURANS

BACKGROUND OF THE INVENTION

This invention relates to the synthesis of 2-nitro-3-phenylbenzofurans substituted by one or more methyl groups, to the use of these compounds as antimicrobial agents, to antimicrobial compositions containing them and to methods for their preparation.

Stoermer (Berichte 44, 1853 (1911)) reports the synthesis of 5-methyl-2-nitro-3-phenylbenzofuran and 6-methyl-2-nitro-3-phenylbenzofuran (named as 4 or 5-methyl-1-nitro-2-phenylcumarons) which fall within the purview of the present invention. However, it is apparent from the analytical and melting point measurements reported there that Stoermer did not obtain those compounds.

DETAILED DESCRIPTION OF THE INVENTION

The invention relates to compounds of the formula

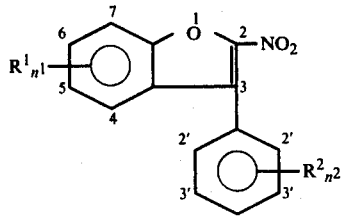

wherein $R^1$ and $R^2$ are alkyl of one to four carbon atoms and $n^1$ and $n^2$ are zero to three and the sum of $n^1$ and $n^2$ is one to five. This invention also relates to the use of these novel compounds as antimicrobial agents and to processes for their preparation.

It has been found that substitution in certain positions of the 3-phenylbenzofuran ring is less desirable with respect to antimicrobial activity versus gram-negative and gram-positive bacteria. For this reason a preferred subclass of the formula

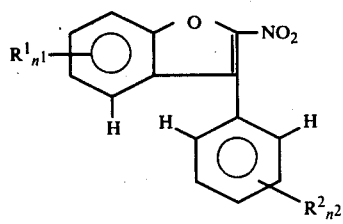

can be designated wherein $R^1$, $R^2$, $n^1$ and $n^2$ are as defined hereinabove and H indicates unsubstituted ring positions. Compounds of the invention containing one or two lower alkyl groups in one or two of the positions 5, 6, 7, 3', or 4' have been found to have good antimicrobial activity, and form a preferred subclass. Compounds wherein $R^1$ and $R^2$ are methyl are presently preferred. The most preferred compounds of the invention are compounds wherein the sum of $n^1$ and $n^2$ is two such as 5,7-dimethyl-2-nitro-3-phenylbenzofuran and 3-(3',4'-dimethylphenyl)-2-nitrobenzofuran.

The antimicrobial activity of the compounds of the present invention can be demonstrated by the known, standard plate dilution method for bacterial susceptibility to antibacterial agents. The culture medium employed permits susceptibility testing of fastidious microorganisms toward antibiotics, sulfonamides and other chemotherapeutic agents. For example, tryptone soy agar (oxoid) of the following composition may be the culture medium.

| Oxiod tryptone | 15 g. |
| Oxoid Soy peptone | 5 g. |
| Sodium chloride | 5 g. |
| Oxiod agar-agar No. 3 | 15 g. |
| Water | 1 liter |

Using this test, the compounds of the invention have been found to have a broad spectrum of activity against gram-positive and gram-negative microorganisms.

The compounds of the invention generally maintain activity against microorganisms either in the absence or presence of ten percent horse serum.

The test procedure used to determine activity as employed in connection with the present invention provides information on the amount of a compound required to give complete inhibition, partial inhibition or no inhibition of microbial growth on the agar plates. In the tests, the selected compound is added to the agar medium to give concentrations of zero, one tenth, one, ten and one hundred milligrams per liter. A series of plates with these concentrations is prepared. Ten percent horse serum is added to one series of such plates. Aliquots of broth culture of each of the species of microorganisms are innoculated onto the agar plates containing the various compound concentrations.

The plates are incubated at 37° C. in a ten percent carbon dioxide atmosphere for 18 to 24 hours. The microbial growth on each plate is read visually, and minimal inhibitory concentrations are recorded.

The microorganisms used for this test are:
1. *Staphylococcus aureus*
2. *Bacillus subtilus*
3. *Pseudomonas aeruginosa*
4. *Escherichia coli*
5. *Streptococcus sp.* *
6. *Asperigillus niger*
7. *Candida albicans*
8. *Mima polymorpha*
9. *Herellea vaginicola*
10. *Klebsiella pneumoniae*
11. *Streptococcus fecaelis*

*Strain isolated from dental caries in rats or hamsters at the National Institute of Dental Health and grown in PFY or APT agar.

All of the compounds of the invention possess antimicrobial activity towards one or more of the above microorganisms.

It will be understood by those skilled in the art that the species used are representative species, as it would be impractical to screen against all bacteria. It is well known in the art that broad spectrum activity versus certain bacterial classes can be predicted on the activity shown against selected representative bacterial species.

All of the compounds of the invention are active against microorganisms in vitro or topically. In vitro activity is useful in itself, since antimicrobial agents may be used for disinfecting and sterilizing, for example medical and dental equipment, as components of disinfecting solutions. In addition, the preferred compounds of the invention are also active in vivo.

The in vivo antimicrobial activity of a test compound is determined against infections produced by *Streptococ-* cus fecaelis and *Staphylococcus aureus* (Smith). The species used is determined by the in vivo antimicrobial spectrum of the compound. Groups of 5 or 10 mice, 18–22 g., are infected intraperitoneally with the test culture. Treatment consists of three oral dosings 1, 6 and 24 hours after infection. All mice are observed for two weeks and deaths recorded at daily intervals. Control groups consist of one infected, nontreated group and other infected groups receiving varying dosages of the reference standard. Reference standards are determined by the nature of the compound being screened (sulfonamide, quinoline, antibiotic, etc.). Cephalosporin or ampicillin is generally used.

It is known to the art that antimicrobial agents are used as growth promoters in various animal and bird species. It is inferred from the antimicrobial activity that the compounds of the invention can be used for this purpose also.

It is also sometimes advantageous to combine the compounds of this invention with other antiprotozoal compounds such as coccidiostats, anthelmintics, antifungals, antibiotics, steroids, or antibacterial agents, or to combine more than one compound described herein in a single composition. Such combinations often provide for an active composition more beneficial than either compound alone.

The compounds of the invention are active against protozoa and would be expected to be active against protozoal diseases such as enterohepatitis, amoebic dysentery, turkey blackhead disease and the like, as well as systemic infections, e.g. local endocarditis, descending upper tract kidney infections, wound infections and eye, ear and sinus infections.

Compounds of the invention are active antiparasitics as shown by activity in laboratory tests versus Trichomonas sp.

Compounds of the invention are active versus anaerobic bacteria as shown in laboratory tests versus Bacteroides sp. and *Clostridium welchii.*

Antitubercular activity has been indicated in laboratory tests versus *Mycobacterium tuberculosis* var. hominis, BCG vaccine strain.

Activity versus *Erwinia amylovora,* a plant bacteria causing disease, has been shown in laboratory tests.

Activity versus Corynebacterium sp. has been detected in laboratory tests.

The acute oral toxicity of the compounds of the invention generally is moderate to low compared with the effective oral dose, and they have a fair to excellent therapeutic ratio. Presently preferred compounds of the invention have a broad spectrum of antimicrobial activity and a good therapeutic ratio ($LD_{50}/ED_{50}$).

The compounds are preferably administered orally as antimicrobial agents but other known methods of administration are contemplated as well, e.g. by subcutaneous injection, intramuscular injection, intravenously, parenterally, topically and the like. Dosages ordinarily fall within the range of about 1 to 100 mg/kg of body weight of the mammal to be treated although oral dosages are not usually above 50 mg/kg and injection dosages are not usually above 25 mg/kg.

Since the active compounds of the invention are both neutral and stable, they are readily formulated by conventional methods known to the art, e.g. with pharmaceutically acceptable diluents, vehicles, carriers, or extending media.

Suitable forms for oral administration include tablets (which may contain anhydrous lactose, microcrystalline cellulose, modified starch, calcium stearate and talc, as well as other pharmaceutically acceptable extending media, diluents, vehicles and conventional compounding agents together with the active antimicrobial agent) and capsules. Liquid formulations, such as solutions or suspensions of the active ingredient in inert carriers, are contemplated for dosage by injection. Suitable carriers and extending media would include water, glucose solution, saline solution, dextran solutions and the like.

The compounds of the invention are prepared by several methods starting with known starting materials or using reaction sequences described hereinbelow which start with known starting materials.

Direct nitration of 3-phenylbenzofurans may be used. The use of dinitrogen tetroxide in acetic acid is sometimes advantageous.

Another useful synthetic route utilizes a reaction sequence wherein the first step is a selective and specific halogenation of the 2-position of the benzofuran ring and the second step is selective replacement of the halogen of the aromatic system by a nitro group.

The halogenation reaction may be bromination or iodination. Bromination is carried out using bromine water or preferably bromine in a suitable solvent such as chloroform or acetic acid. The bromo compound may be isolated or may be used without isolation. Isolation may be carried out by extraction, precipitation by the addition of a solvent such as water which precipitates the product, evaporation of volatile reaction components and the like. Iodination is carried out with molecular iodine in the presence of yellow mercuric oxide in an inert solvent such as benzene.

Selective replacement of the 2-halo substituent is carried out using selected nitrating agents, such as sodium nitrite with 70% nitric acid solution in acetic acid, dinitrogen tetroxide in an inert solvent such as chloroform or acetic acid or a mixture of sodium nitrite and other strong acids in acetic acid. In the first instance preferably about two moles of sodium nitrite per mole of benzofuran is included and one to three milliliters of 70% nitric acid per gram of nitrite is used. Another component of the nitration reagent is glacial acetic acid as solvent. About four to twenty milliliters of acetic acid per gram of 2-halobenzofuran derivative is used, depending on its solubility. It is desired to maintain the dissolution of the 2-halobenzofuran derivative, and the amount of acetic acid and the reaction temperature is adjusted to achieve this result readily. The reaction temperature is about 25° to 100° C., and preferably about 60° to 80° C. to aid removal of bromine produced.

It has been found that a mixture of sodium nitrite, nitric or sulfuric acid and acetic acid in the presence of an olefin will also nitrate the 2-halobenzofuran derivatives successfully in the 2-position, and this is a preferred procedure. The 2-halobenzofuran derivative is dissolved in acetic acid to maintain solution (up to 20 ml per gram required) and concentrated nitric or sulfuric acid is added. Sodium nitrite is then added, from two to five moles of nitrite per mole of benzofuran derivative being used. The amount of concentrated nitric or sulfuric acid added is from one to three milliliters per gram of sodium nitrite. The reaction temperature is about 10° to 100° C. Presumably other metal nitrites than sodium nitrite as potassium nitrite are equivalent and could be used alternatively.

A combination of dinitrogen tetroxide in an inert solvent in the presence of an alkene is the presently preferred nitration method. Acetic acid is a preferred solvent because it dissolves the 2-halobenzofuran derivative and is inert to dinitrogen tetroxide. Two to five liters of acetic acid per mole of benzofuran derivative are generally used. At least one mole of dinitrogen tetroxide per mole of benzofuran is used. The exact amount depends on the rate of reaction desired, the extent of volatilization and other physical losses and the amount of competitive addition to the added olefin. The temperature of these reactions is generally about 0° to 80° C., about 10° to 80° C. for bromine exchange and about 0° to 25° C. for iodine exchange.

An alkene is preferably used when the 2-halobenzofuran derivative is a bromo derivative, since it removes the elements of $BrNO_2$ and minimizes bromination as a side reaction. Cyclohexene is satisfactory for this use. Preferably one mole of alkene per mole of dinitrogen tetroxide is used. The olefin is chosen to be less reactive to $N_2O_4$ than the benzofuran but more reactive to $BrNO_2$ than is the benzofuran. An acidic olefin, e.g. 2-cyclohexene carboxylic acid or itaconic acid, is advantageous with the neutral products of this invention.

When 2-iodobenzofurans are used, only one-half mole of $N_2O_4$ is theoretically required in the absence of olefin. Olefin is not required since the iodine is generally unreactive to the benzofuran under the conditions used.

The synthetic processes described hereinabove are illustrative of procedures useful for obtaining the compounds of this invention but are not intended to be limiting. The following examples will more fully illustrate the preparation of the compounds of the invention using these processes.

EXAMPLE 1

To a solution of 216 g (2.0 mole) of p-cresol and 300 g (2.18 mole) of potassium carbonate in 1.2 l of acetone is added in two portions (about one hour apart) 400 g (2.0 mole) of alpha-bromoacetophenone. The mixture is then heated to its reflux temperature and maintained at reflux for about 20 hours. The reaction mixture is filtered, and the residue is extracted with a 1:1 mixture of acetone and ethanol. The filtrate is diluted with water and a precipitate crystallizes. This solid is combined with the acetone-ethanol extracts and dissolved in 1.8 l of 1:1 diethyl ether-dichloromethane. The solution is washed with cold dilute sodium hydroxide solution, water and saturated sodium chloride solution, then dried over anhydrous magnesium sulfate. The mixture is filtered and the filtrate evaporated to dryness under vacuum. The residue is taken up in 1:1 ethanol-hexane and the product is isolated by filtration. The solid is alpha-(4-methylphenoxy)acetophenone, m.p. 63°–64° C.

A mixture of 193 g of alpha-(4-methylphenoxy)acetophenone and 2 kg of polyphosphoric acid is heated at 60° to 72° C. for about one hour, the poured into an ice-water mixture. The mixture is extracted with dichloromethane, the extracts are dried, then concentrated to provide crude 5-methyl-3-phenylbenzofuran as an oil.

To a solution of 119 g (0.816 mole) of 5-methyl-3-phenylbenzofuran in 1 l. of chloroform at 20° to 25° C. is added 143.5 g (0.895 mole) of bromine. The mixture is evaporated under vacuum and the residue is dissolved in diethyl ether. The ether solution is washed with water, 10% sodium bicarbonate solution and saturated sodium chloride solution. The dried mixture is filtered and the filtrate is evaporated under vacuum. The residue is suspended in hot petroleum ether, then the mixture is cooled to provide solid 2-bromo-5-methyl-3-phenylbenzofuran, m.p. 52°–57° C.

To a solution of 25 g (0.0875 mole) of 2-bromo-5-methyl-3-phenylbenzofuran and 16.5 g of cyclohexene-4-carboxylic acid in 150 ml of acetic acid is added 17.5 g of sodium nitrite, then 17.5 ml of nitric acid is added dropwise with stirring. The mixture is stirred at about 25° C. for about three hours, then poured onto ice. The mixture is then extracted with diethyl ether. The ether solution is washed with 10% sodium bicarbonate solution, saturated sodium carbonate solution and dried. The dried solution is evaporated under vacuum to provide a yellow residue. The residue is recrystallized from carbon tetrachloride, then cyclohexane to provide yellow crystals of 5-methyl-2-nitro-3-phenylbenzofuran, m.p. 144.5°–146° C.

| Analysis: | %C | %H | %N |
|---|---|---|---|
| Calculated for $C_{15}H_{11}NO_3$: | 71.1 | 4.38 | 5.5 |
| Found: | 70.9 | 4.2 | 5.6 |

EXAMPLE 2

Using an alternative condensation, equimolar amounts of m-cresol and alpha-bromoacetophenone are refluxed in benzene in the presence of potassium carbonate with azeotropic removal of water to provide alpha-(3-methylphenoxy)acetophenone.

A mixture of 4 parts by weight polyphosphoric acid to 1 part alpha-(3-methylphenoxy)acetophenone is heated at about 125° C. for several hours, then poured into an ice-water mixture. The solid product isolated by filtration is a mixture of (about 2:3) 4-methyl-3-phenylbenzofuran and 6-methyl-3-phenylbenzofuran. This mixture is treated with bromine in dichloromethane to provide a mixture of 2-bromo-4-methyl-3-phenylbenzofuran and 2-bromo-6-methyl-3-phenylbenzofuran which is fractionally recrystallized. One fraction is 1:3, 6 isomer to 4-isomer which when chromatographed on a silica gel column, eluting with large volumes of petroleum ether provides early fractions with about 85% 4-methyl isomer. Another fraction is 7:1, 6-isomer to 4-isomer. This fraction is used in the reaction of Example 4. The structure and purity of the isomers is established by analysis of the nuclear magnetic resonance spectra.

To a solution of 2.9 g (0.01 mole) of 85% 2-bromo-4-methyl-3-phenylbenzofuran and 1.65 g (0.013 mole) of cyclohexene-4-carboxylic acid in 25 ml of chloroform is added rapidly 1.1 g (0.012 mole) of dinitrogen tetroxide dissolved in a minimum volume of chloroform. The initially exothermic reaction is stirred for about 16 hours without external heating. An equal volume of water is added and the mixture is stirred thoroughly. The organic layer is washed with water, saturated sodium bicarbonate solution and again with water, then dried. After evaporation of solvent, the residue slowly crystallizes, and is recrystallized from 3:1 hexane-benzene, then twice recrystallized from 1:1 hexane-benzene with treatment by decolorizing charcoal. The product is yellow crystals of 4-methyl-2-nitro-3-phenylbenzofuran, m.p. 100° to 102° C.

| Analysis: | %C | %H | %N |
|---|---|---|---|
| Calculated for $C_{15}H_{11}NO_3$: | 71.1 | 4.4 | 5.5 |

| Analysis: | | %C | %H | %N |
|---|---|---|---|---|
| | Found: | 71.2 | 4.0 | 5.4 |

The isomeric purity is established by nuclear magnetic resonance spectral analysis.

EXAMPLE 3

Equimolar amounts of o-cresol and alpha-bromoacetophenone are refluxed in benzene in the presence of potassium carbonate to provide alpha-(2-methylphenoxy)acetophenone.

A mixture of 4 parts by weight polyphosphoric acid to 1 part alpha-(2-methylphenoxy)acetophenone is heated at about 80° C. for several hours, then poured into an ice-water mixture. The liquid product isolated by filtration is 7-methyl-3-phenylbenzofuran.

To a solution of 60 g (0.288 mole) of 7-methyl-3-phenylbenzofuran in 500 ml of dichloromethane is added dropwise 46.1 g (0.288 mole) of bromine diluted with 20 ml of dichloromethane. The solution is stirred for several hours until the evolution of hydrogen bromide gas ceases. The mixture is washed with 10% sodium bicarbonate solution, then with water and dried. After evaporation, the purple oil residue is crude 2-bromo-7-methyl-3-phenylbenzofuran.

A solution of 82.7 g (0.288 mole) of 2-bromo-7-methyl-3-phenylbenzofuran and 18.1 g (0.144 mole) of cyclohexene-4-carboxylic acid in 500 ml of acetic acid is treated over about 30 minutes with 13.2 g (0.144 mole) of dinitrogen tetraoxide in 20 ml of acetic acid. After about two hours 21.8 g (0.173 mole) of cyclohexene-4-carboxylic acid and 15.9 g (0.173 mole) of dinitrogen tetroxide in 25 ml of acetic acid is added. After about 5 additional hours the reaction mixture is poured into cold water to give the crude product as a gum. Trituration with diethyl ether gives a solid which is recrystallized from cyclohexane and carbon tetrachloride to provide yellow solid 7-methyl-2-nitro-2-phenylbenzofuran, m.p. 122°–126° C.

| Analysis: | %C | %H | %N |
|---|---|---|---|
| Calculated for $C_{15}H_{11}NO_3$: | 71.1 | 4.38 | 5.4 |
| Found | 70.5 | 4.2 | 5.3 |

EXAMPLE 4

To a stirred solution of 4 g (0.014 mole) of 2-bromo-6-methyl-3-phenylbenzofuran in 50 ml of acetic acid and 50 ml of chloroform is added 1.8 g (0.015 mole) of cyclohexene-4-carboxylic acid and a solution of 1.4 g (0.015 mole) of dinitrogen tetroxide in 10 ml of acetic acid. After sitting for about 16 hours the mixture is poured into water. This mixture is extracted with chloroform and the extracts are washed with water and 10% sodium bicarbonate solution and dried. Evaporation of the solvent and recrystallization of the residue from cyclohexane provides yellow crystals of 6-methyl-2-nitro-3-phenylbenzofuran, m.p. 142°–144° C.

| Analysis: | %C | %H | %N |
|---|---|---|---|
| Calculated for $C_{15}H_{11}NO_3$: | 71.1 | 4.38 | 5.5 |
| Found: | 70.8 | 4.3 | 5.4 |

EXAMPLE 5

Using the method described in Example 1, 2,4-dimethylphenol is reacted with alpha-bromoacetophenone to provide alpha-(2,4-dimethylphenoxy)acetophenone.

Using the method described in Example 1, alpha-(2,4-dimethylphenoxy)acetophenone is cyclized in polyphosphoric acid at 55° C. to provide 5,7-dimethyl-3-phenylbenzofuran as an orange oil.

A solution of 5.6 g (0.025 mole) of 5,7-dimethyl-3-phenylbenzofuran in 100 ml of acetic acid is stirred while adding dropwise over 2 hours 2.8 g (0.030) mole of dinitrogen tetroxide in 25 ml of acetic acid. The mixture is poured into cold water to separate the product as a green gum. The product is taken up in diethyl ether, the solution is washed with water, 10% sodium bicarbonate, water and saturated sodium chloride solution and dried. After evaporation the residue is chromatographed on silica gel, eluting with carbon tetrachloride and 1:1 chloroform-carbon tetrachloride. An early fraction of yellow solid is recrystallized from ethanol-water. A purified sample of this product, 5,7-dimethyl-2-nitro-3-phenylbenzofuran, has m.p. 131°–132.5° C.

| Analysis: | %C | %H | %N |
|---|---|---|---|
| Calculated for $C_{16}H_{13}NO_3$: | 71.9 | 4.9 | 5.2 |
| Found: | 71.7 | 4.8 | 5.1 |

EXAMPLE 6

Using the method described in Example 1, phenol is reacted with alpha-bromo-(3,4-dimethyl)acetophenone to give alpha-phenoxy-(3,4-dimethyl)acetophenone.

Using the method described in Example 1 alpha-phenoxy-(3,4-dimethyl)acetophenone is cyclized in polyphosphoric acid at 55° C. to 3-(3',4'-dimethylphenyl)benzofuran isolated as a dark oil.

To a solution of 10.5 g (0.047 mole) of 3-(3',4'-dimethylphenyl)benzofuran in 150 ml of dichloromethane is added 4.9 g (0.060 mole) of sodium acetate followed by dropwise addition over 2.5 hours of 7.5 (0.047 mole) of bromine in 25 ml of dichloromethane. The mixture is stirred for 2.5 hours additional, then washed with water, 10% sodium bicarbonate, water and saturated sodium chloride and dried. After evaporation the residue is an orange oil, crude 2-bromo-3-(3',4'-dimethylphenyl)benzofuran.

To a solution of 12.4 g (0.041 mole) of 2-bromo-3-(3',4'-dimethylphenyl)benzofuran in 400 ml of acetic acid is added 7.8 g (0.062 mole) of cyclohexene-4-carboxylic acid and a solution of 5 g (0.062 mole) of dinitrogen tetroxide in 25 ml of acetic acid. After stirring for about 16 hours the mixture is poured into cold water to give a gummy solid. The solid is collected, washed with water and dissolved in diethyl ether. The ether solution is washed with water, 10% sodium bicarbonate solution and saturated sodium chloride solution, then dried. Evaporation provides a residue which is dissolved in carbon tetrachloride and chromatographed on silica gel, eluting with carbon tetrachloride and combining the fractions consisting of chiefly one component according to thin layer chromatography. The solid is recrystallized from aqueous ethanol, then from isopropanol to provide yellow solid 3-(3',4'-dimethylphenyl)-2-nitrobenzofuran, m.p. 125°–133° C. which is about 90% pure, containing about 10% of monobromo-3-(3',4'-dimethylphenyl)-2-nitrobenzofuran.

EXAMPLE 7

Using the procedure of Example 3 and starting with p-cresol and 4'-methyl-2-bromoacetophenone one obtains 5-methyl-3-(4-methylphenyl)-2-nitrobenzofuran.

EXAMPLE 8

Using the procedure of Example 3 and starting with 4-ethylphenol and alpha-bromoacetophenone one obtains 5-ethyl-2-nitro-3-phenylbenzofuran.

EXAMPLE 9

To a stirred mixture of 12.9 g (0.062 mole) of 7-methyl-3-phenylbenzofuran in 14 ml of benzene at 60° C. is added 10.8 g (0.050 mole) of mercuric oxide and 15.7 g (0.062 mole) of iodine, alternately in small batches, over one hour. Stirring is continued for an additional thirty minutes, then the mixture is allowed to cool to about 25° C. The mixture is diluted with benzene and filtered. The filtrate is concentrated to dryness yielding a red oil. The oil is chromatographed on silica gel, eluting with carbon tetrachloride and then 1:1 chloroform-carbon tetrachloride. A yellow oil is obtained from the early fractions and is found to be 2-iodo-7-methyl-3-phenylbenzofuran by infrared and nuclear magnetic resonance spectral analysis.

EXAMPLE 10

To a stirred solution of 5.0 g (0.015 mole) of 2-iodo-7-methyl-3-phenylbenzofuran from Example 9 in 100 ml of acetic acid is added 2.8 g (0.022 mole) of cyclohexene-4-carboxylic acid, then dropwise 2.0 g (0.022 mole) of dinitrogen tetroxide in 10 ml of acetic acid. The mixture is poured into cold water, then extracted with diethyl ether. The ether extracts are washed with water, 5% sodium hydroxide solution, water and saturated sodium chloride solution and dried. The extracts are then concentrated to provide a solid residue which is recrystallized from aqueous ethanol to provide yellow crystals of 7-methyl-2-nitro-3-phenylbenzofuran, m.p. 122°-127° C., which is shown to be identical to the product of Example 2 by its infrared spectrum.

EXAMPLE 11

To a stirred solution of 5.0 g (0.015 mole) of 2-iodo-7-methyl-3-phenylbenzofuran from Example 9 in 100 ml of acetic acid is added dropwise 2.0 g (0.022 mole) of dinitrogen tetroxide in 10 ml of acetic acid. After stirring one hour the mixture is poured into cold water, then extracted with diethyl ether. The ether extracts are washed with water, 10% sodium bisulfite solution, water and saturated sodium chloride solution and dried. Concentration gives a tan powder which is recrystallized from aqueous ethanol to give yellow crystals of 7-methyl-2-nitro-3-phenylbenzofuran, m.p. 123°-126° C. This product is identical to the product of Example 2 according to comparative infrared spectral analysis.

EXAMPLE 12

Using the procedure of Example 3 and staring with 2,4-dimethylphenol and alpha-bromo-3,4-dimethylacetophenone one obtains 5,7-dimethyl-3-(3',4'-dimethylphenyl)-2-nitrobenzofuran.

EXAMPLE 13

Using the procedure of Example 3 and starting with 2,3,4-trimethylphenol and alpha-bromoacetophenone one obtains 2-nitro-3-phenyl-5,6,7-trimethylbenzofuran.

EXAMPLE 14

Using the procedure of Example 3 and starting with 2,3,4-trimethylphenol and alpha-bromo-3,4-dimethylacetophenone one obtains 3-(3',4'-dimethylphenyl)-2-nitro-5,6,7-trimethylbenzofuran.

The following example is used to illustrate the antimicrobial activity of some of the compounds of the invention against selected microorganisms. The test used is the standard plate dilution method (serum free) described hereinabove.

EXAMPLE 15

| Compound of Example No. | Concentration at which inhibition is seen (mcg/ml) | | | |
|---|---|---|---|---|
| | Streptococcus sp. | E. coli | Enterococcus | Bacillus subtilis |
| 1 | 1 | 1 | 1 | 1 |
| 2 | 1 P | 10 P | 100 | — |
| 3 | 10 | 1 | 1 | 1 |
| 4 | 1 | 0.1 P | 1 | 0.1 |
| 5 | 1 | 1 P | 1 | 1 |
| 6 | 1 | 1 P | 1 | 1 |

P in the table and below indicates partial inhibition, expressed in micrograms per milliliter (mcg/ml).

The compound of Example 1 has also shown activity against the following microorganisms: *Staphylococcus aureus*, serum free MIC (minimum inhibitory concentration, mcg/ml) of 1, with serum 1 P; *Pseudomonas aeruginosa*, serum free 100 P; Bacteroides sp., 27 mm zone of inhibition at 40 mcg/ml; Clostridium sp. 23 mm zone of inhibition at 40 mcg/ml; Mycobacterium sp. MIC of 10, 1 P; Erwinia amylovora, 13 mm zone of inhibition at 40 mcg/ml; Corynebacterium sp., zone of inhibition at 40 mcg/ml is 11 mm.

What is claimed is:
1. A compound of the formula

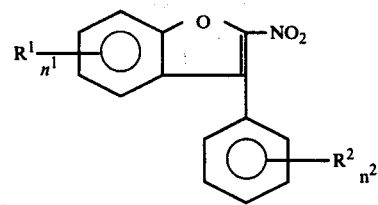

wherein $R^1$ and $R^2$ are each alkyl groups containing from one to four carbon atoms and $n^1$ and $n^2$ are each 0–2, provided that the sum of $n^1$ and $n^2$ is 2.

2. A compound according to claim 1 having the formula

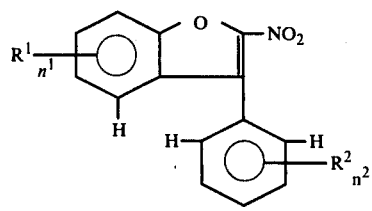

3. A compound according to claim 1 wherein $R^1$ and $R^2$ are methyl.

4. The compound 5,7-dimethyl-2-nitro-3-phenylbenzofuran.

5. The compound 3-(3',4'-dimethylphenyl)-2-nitrobenzofuran.

6. An antimicrobial composition comprising an antimicrobially effective amount of a compound of the formula

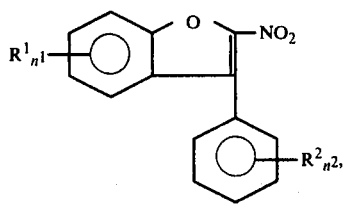

wherein $R^1$ and $R^2$ are each alkyl groups containing from 1 to 4 carbon atoms and $n^1$ and $n^2$ are each 0–3, provided that the sum of $n^1$ and $n^2$ is 1–5, dispersed in a pharmaceutically acceptable extending medium.

7. A method for arresting or inhibiting the growth of microorganisms comprising contacting said microorganisms with a compound of the formula

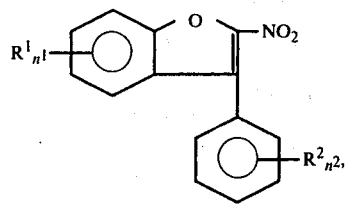

wherein $R^1$ and $R^2$ are each alkyl groups containing from 1 to 4 carbon atoms and $n^1$ and $n^2$ are each 0–3, provided that the sum of $n^1$ and $n^2$ is 1–5, in an amount sufficient to inhibit the growth of said microorganisms.

8. A method according to claim 7 wherein the compound has the formula

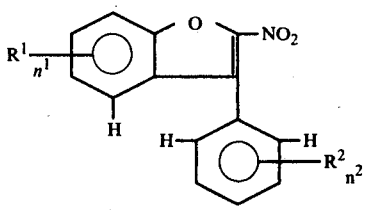

wherein $R^1$ and $R^2$ are each alkyl groups containing from 1 to 4 carbon atoms and $n^1$ and $n^2$ are each 0–3, provided that the sum of $n^1$ and $n^2$ is 1–5.

9. A method according to claim 7 wherein $R^1$ and $R^2$ are methyl.

10. A method according to claim 8 wherein the sum of $n^1$ and $n^2$ is 1–2.

11. A method according to claim 10 wherein the sum of $n^1$ and $n^2$ is 2.

12. A method for arresting or inhibiting the growth of microorganisms comprising contacting said microorganisms with 5,7-dimethyl-2-nitro-3-phenylbenzofuran in an amount sufficient to inhibit the growth of said microorganisms.

13. A method for arresting or inhibiting the growth of microorganisms comprising contacting said microorganisms with 3-(3',4'-dimethylphenyl)-2-nitrobenzofuran in an amount sufficient to inhibit the growth of said microorganisms.

* * * * *

UNITED STATES PATENT AND TRADEMARK OFFICE
CERTIFICATE OF CORRECTION

PATENT NO. : 4,141,990

DATED : February 27, 1979

INVENTOR(S) : Robert A. Scherrer

It is certified that error appears in the above-identified patent and that said Letters Patent are hereby corrected as shown below:

Column 2, in the table:

"Oxiod tryptone" should read -- Oxoid tryptone -- .

"Oxiod agar-agar No. 3" should read -- Oxoid agar-agar No. 3 -- .

Column 8, line 43, after "7.5" insert -- g -- .

Signed and Sealed this

Fourteenth Day of August 1979

[SEAL]

Attest:

Attesting Officer

LUTRELLE F. PARKER

Acting Commissioner of Patents and Trademarks